United States Patent [19]

Tomlinson et al.

[11] 4,066,745
[45] Jan. 3, 1978

[54] DENTIFRICE

[75] Inventors: Kenneth Tomlinson, Bramhall; Michael Harrison, New Castle upon Tyne, both of England

[73] Assignee: Colgate-Palmolive Company, New York, N.Y.

[21] Appl. No.: 661,238

[22] Filed: Feb. 25, 1976

Related U.S. Application Data

[60] Division of Ser. No. 446,453, Feb. 27, 1974, Pat. No. 3,946,108, which is a continuation of Ser. No. 202,664, Nov. 26, 1971, abandoned.

[51] Int. Cl.² ............................................. A61K 7/16
[52] U.S. Cl. ...................................................... 424/49
[58] Field of Search .................................... 424/49-58

[56] References Cited

U.S. PATENT DOCUMENTS

| 2,059,396 | 11/1936 | Ripert | 424/49 |
| 3,011,950 | 12/1961 | Mehaffey | 424/49 |
| 3,538,230 | 11/1970 | Pader et al. | 424/50 |
| 3,551,559 | 12/1970 | Miles | 424/49 |
| 3,574,823 | 4/1971 | Roberts et al. | 424/50 |
| 3,711,604 | 1/1973 | Colodney et al. | 424/52 |
| 3,728,446 | 4/1973 | Roberts et al. | 424/49 |
| 3,840,657 | 10/1974 | Norfleet | 424/49 |
| 3,946,108 | 3/1976 | Tomlinson et al. | 424/49 |

OTHER PUBLICATIONS

Watson, J. Soc. Cosmetic Chemists 21:469, (1970).
Neumann et al., J. Soc. Cosmetic Chemists 21:255–258, (1970).
Plank J. Colloid, Sci. 2:413–427, (1947).
Plank et al., J. Colloid Sci. 2:399–412, (1947).

Primary Examiner—Shep K. Rose
Attorney, Agent, or Firm—Robert L. Stone; Murray M. Grill; Herbert S. Sylvester

[57] ABSTRACT

Extrudible visually clear gel dentifrice containing distributed therein visible bubbles of gas, said dentifrice having a vehicle of viscosity sufficient to maintain the bubbles suspended therein.

7 Claims, No Drawings

DENTIFRICE

This application is a division of Ser. No. 446,453, filed Feb. 27, 1974, now U.S. Pat. No. 3,946,108, issued Mar. 23, 1976, which is a continuation of Ser. No. 202,664, filed Nov. 26, 1971, now abandoned.

This invention relates to dentifrices. More particularly, it relates to dentifrices which are visually substantially clear and which contain visible gas bubbles.

Although most dentifrices sold throughout the world are opaque, usually due to their contents of insoluble and opaque polishing agents, it has been found that some consumers decidedly prefer visually clear, translucent or transparent dentifrices. When some clear dentifrice liquids were marketed many years ago they suffered from the absence of a suitable polishing agent and teeth brushed with such dentifrices accumulated deposits of tartar, films and stains, despite the presence in the dentifrice of excellent detergents. Recently, this disadvantage has been overcome by the introduction of polishing agents which can be incorporated in dentifrices and which permit the dentifrice to be visually clear, even when a substantial proportion of polishing agent is present. Such polishing agents are transparent in themselves and possess indexes of refraction in the same range as the index of refraction of the vehicle and the balance of the dentifrice composition. Accordingly, there is no disturbance of the path of light passing through the polishing agent particle and the gel dentifrice appears to be clear to a viewer.

It has been noted that visually clear dentifrices, although attractive to many viewers, also result in some consumers having an unfavorable reaction about the properties of the dentifrice. To some the smooth, transparent product does not give the impression of being an effective cleaner. Yet, some of these consumers and others prefer a clear product which is periodically interrupted by different contained materials. Such give the product more "character", make it readily distinguishable from other dentifrices and make it even more attractive in appearance. Most materials that may be suspended in a dentifrice are palpable, insoluble or gritty and may not be acceptable to the consumer. On the other hand, dispersions of differently colored dentifrice portions or of gases in the main body of the dentifrice are not objectionable. Although the colors of dispersed solid materials or gels may run, the gases maintain a distinctive appearance in the dentifrice, indefinitely in the products of this invention. They also possess other advantages, since it is possible to adjust the density of the product and the solids/extruded inch of dentifrice by inclusion in the formula of different proportions of gases.

During the production of dentifrices and other thick products in which solid materials are dispersed in a liquid medium, air may sometimes by dissolved in the medium or entrapped in the product. Such air is not desirable in dentifrices, especially in clear dentifrices, since it is apparent to a consumer and may cause the product to be unattractive. This is so because the air will often be unevenly distributed, of such particle sizes as to make the product appear cloudy, or will be of irregular shapes, which are less attractive than perfect spheres. Accordingly, such dispersed gas may be intentionally removed from dental preparations. Now, however, by the method of the present invention, regularly distributed bubbles of desired shape and size are produced and the appearance of clear gel dentifrices is improved by their presence.

In accordance with the present invention, a method for manufacturing a dentifrice containing gas bubbles comprises making a gas-free or substantially gas-free viscous, extrudible paste or gel dentifrice comprising a polishing agent, a gelling agent and a vehicle, and mixing with such dentifrice bubbles of gas of a size in the range of 0.1 to 4 millimeters diameter of an equivalent sphere so that there are from 2 to 100 such bubbles per cubic centimeter of dentifrice, the dentifrice being of a viscosity sufficient to maintain the bubbles suspended therein. The preferred products made are visually clear gel dentifrices containing distributed therein visible bubbles of gas of diameters in the 1 to 4 millimeter range and distributed throughout the dentifrice so that there are from 2 to 20 bubbles per cubic centimeter of dentifrice, which dentifrice comprises a polishing agent, gelling agent and a vehicle and is of a viscosity sufficient to maintain the bubbles suspended therein. The clear gel dentifrices of this invention include polishing agents, gelling agents and vehicles, usually with a detergent or foaming agent present. Other adjuvants are usually present to contribute color flavor, antibacterial, preservative, buffering, and other desirable effects, and an insoluble gas, i.e., a gas which will not dissolve objectionably in the dentifrice medium, although some of the same gas may already be dissolved therein, is present to create the dispersed bubble or sphere effect in the dentifrice.

The polishing agents for visually clear dentifrices are usually finely divided water insoluble powdered materials of particle sizes such that they pass a 140 mesh screen, U.S. Standard Sieve Series. Preferably, the particles are less than 100 or 65 microns in diameter, are substantially spherical or of matching lengths and widths, are transparent and have an index of refraction like that of the rest of the dentifrice medium. Preferably, the particles are of 1 to 40 microns and most preferably from 2 to 20 microns in particle size diameter and the distribution of particle sizes will be normal over the described or narrower ranges. Among the most useful polishing agents that satisfy these conditions are complex aluminosilicates such as sodium aluminosilicate, and silica xerogels, which are often partially, e.g., 20% hydrated. Such materials have indexes of refraction in the range of 1.4 to 1.5, preferably 1.44 to 1.48 and usually 1.46 or 1.47. The silica xerogel or other colloidal or amorphous silicas or silicon hydrides often have surface areas of from 200 to 1,000 square meters/gram and generally the surface area will be from 200 to 500 sq. m./g. Such area per weight ranges are desirable for the polishing agents of this invention. The colloidal silicas described are available from the Davison Chemical Division of Grace Corp., under the name Syloid. The Syloid xerogels and hydrogels are identified by numerals and it has been found that Syloids 63, 72 and 74 are useful in the practice of the present invention, as are related materials sold as Santocels, e.g., Santocel 100. The bulk densities of such compounds are usually from about 0.05 to 0.4 gram/cubic centimeter and they are found to be readily and uniformly suspandable in gel dentifrices. Among the other excellent polishing agents for the present applications are synthetic, amorphous complex metal aluminosilicate salts, particularly alkali metal salts such as the sodium salts, and alkaline earth metal salts, such as the calcium salt. Such materials contain up to about 20% by weight of moisture and up to about 10% by weight of an alkali metal or alkaline earth metal oxide. They are available under the DeGussa tradename, e.g., DeGussa P820. The complex aluminosilicate salts, which appear to contain interbonded silica and alumina, having Al—O—Si bonds, are described by Tamele in "Chemistry of the Surface and Activity of the Aluminum-Silica Cracking Catalysts" appearing in *Discussions of the Faraday Society* No. 8, pages 270–279 (1950) particularly at page 273, and in the article by Milliken et al. entitled "The Chemical Characteristics and Structure of Cracking Catalysts" at pages 279–290 in the same publication, particularly in the paragraph bridging pages 284 and 285.

Other clear polishing agents or agents which become clear in a particular medium may also be employed. The major requirements are that the refractive index should match that of the other constituents and the materials should be of a suitable hardness and a particle size similar to those mentioned so as to give good polishing action without scratching.

The methods of this invention, while particularly appropriate for making bubbled clear gel dentifrices, may also be employed in uniformly bubbling opaque dentifrices for density control, and in such cases the various polishing agents employed in such preparations may be present. As examples of these there may be mentioned various insoluble, preferably impalpable phosphates, e.g., dicalcium phosphate, tricalcium phosphate, insoluble sodium metaphosphate, magnesium phosphate, calcium pyrophosphate; crystalline silica; colloidal silica; aluminum hydroxide; alumina trihydrate; magnesium carbonate; calcium carbonate; bentonite; talc; calcium silicate; calcium aluminate; aluminum oxide, and aluminum silicate. The various polishing agents are described in standard handbooks such as Cosmetics: Science and Technology, by Sagarin, Second Printing, 1963, published by Interscience Publishers, Inc.

The gelling agents which may be useful to gelate or thicken the dentifrices of the present invention are known in the art and include the natural and synthetic gums and gum-like materials, such as alkali metal carboxymethyl cellulose, e.g., sodium carboxymethyl cellulose; hydroxyethyl carboxymethyl cellulose; polyvinyl pyrrolidone; Irish moss; gum tragacanth; hydroxypropyl methyl cellulose; methyl cellulose; starches; starch glycolates; polyvinyl alcohol; alginates; carbo bean gums; hydrophilic colloidal carboxyvinyl polymers, such as those sold under the trademarks Carbopol 934 and Carbopol 940; diatomaceous earths; bentonite and other natural clays; proteinaceous materials, either animal-or vegetable-derived; synthetic inorganic clays such as the silicated clays sold under the trademarks Laponite CP and Laponite SP and having the formula $[Si_8Mg_{5.1}Li_{0.6}H_{7.6}O_{24}]^{0.6-}Na_{0.6}{}^+$ and colloidal silicas, such as the aerogels, including Syloids 244 and 266 and Aerosil D-200; and the pyrogenic silicas, sold as Cab—O—Sils. The gelling materials employed are gelable with polyhydric alkanols, such as glycerol and sorbitol, and with water and lower alkanols. Normally, the gels are formed when at least some water is present. The liquid or vehicle portion of the composition may include water, lower alkanol and polyhydric alkanol. Although propylene glycol may be employed, it is normally preferred that the major vehicle components should be polyhydric alcohols such as glycerine, sorbitol or glycerine-sorbitol mixtures, with some water. Such vehicles have refractive indexes in the 1.44 to 1.48 range and therefore, are excellent for use with silica xerogels or complex aluminosilicate polishing agents.

Although not absolutely necessary, it is usually desirable to have present in the dentifrices organic surface active agents, generally for their properties as detergents or foaming agents. The cationic detergents may be employed but are usually omitted from the composition in favor of anionic, nonionic and amphoteric surface active agents. Of these, the anionics are the most preferred. The anionic detergents or foaming agents will include long chain fatty or poly-lower alkoxy groups plus hydrophilic radicals. They will be usually in the forms of salts, especially water soluble salts of alkali or alkaline earth metals. Among the useful anionic detergents may be mentioned the higher fatty acid monoglyceride monosulfates, such as the sodium salts of the monosulfates of the monoglycerides of hydrogenated coconut oil fatty acids; higher alkyl sulfates, such as sodium lauryl sulfate; higher alkyl aryl sulfonates, such as sodium linear dodecyl benzene sulfonate; olefin sulfonates, such as sodium higher olefin sulfonate in which the olefin group is of 12 to 21 carbon atoms; higher alkyl sulfoacetates; higher fatty acid esters of 1,2-dihydroxypropane sulfonates; the substantially saturated higher aliphatic acyl amides of lower aliphatic aminocarboxylic acid compounds, such as those having 12 to 16 carbon atoms in the fatty alkyl or acyl radicals; higher alkyl poly-lower alkoxy (of 10 to 100 alkoxies) sulfates; higher fatty acid soaps, and the like. In this specification, for convenience and ease of presentation, the soluble soaps are considered to be synthetic organic detergents. Examples of the amides mentioned are N-lauroyl sarcosine and the sodium, potassium and ethanolamine salts of N-lauroyl-, N-myristoyl- or N-palmitoyl sarcosines. In the above descriptions, "higher" refers to chain lengths of 12 to 22 carbon atoms, preferably from 12 to 18 carbon atoms and most preferably, from 12 to 16 carbon atoms. Lower means 2 to 4 carbon atoms, preferably 2 to 3 carbon atoms and most preferably, 2 carbon atoms. In a broader description of the useful anionic detergents, they are sulfuric reaction products which include long chain hydrophobic groups and hydrophilic radicals. For further descriptions, see the text, *Surface Active Agents*, Vol. II (1958) by Schwartz, Perry and Berch. The nonionics include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; the mixed co-polymers of ethylene oxide and propylene oxide, sold as Ucons; and various other well known nonionics derived from fatty alcohols or acids and polyethylene oxide. The amphoteric or ampholytic agents and cationics include quaternized imidazole derivatives, such as "Miranols", e.g., Miranol $C_2M$; and cationic germicides, such as di-isobutyl-phenoxyethoxyethyl dimethyl benzyl ammonium chloride; benzyl dimethyl stearyl ammonium chloride; and tertiary amines having a higher fatty alkyl group and two polyoxyethylene groups attached to the nitrogen thereof. Of course, reference to the mentioned text will indicate other suitable surface active detergent and foaming constituents which may be employed in the dentifrice compositions. Mixtures of the surface active materials may be used for adjustment of properties and to obtain the most desired effects. In such mixtures, it will generally be desirable to avoid utilizing both anionics and cationics together.

Various adjuvants may be employed in the present dentifrices. Perhaps the most important of these are flavoring agents, which will normally be essential oils but may also include various flavoring aldehydes, esters, alcohols and similar materials, known in the art. Examples of the essential oils include oils of spearmint, peppermint, wintergreen, sassafras, clove, sage, eucalyptus, marjoram, cinnamon, lemon, lime and orange. Solvents may sometimes be present to solubilize the flavoring agents and to have a desirable processing effect in carrying out the methods of this invention wherein entrapped gases are initially removed from the product before a controlled addition of gas bubbles is effected. Some of the solvents have flavoring properties and of these, chloroform is sometimes employed because it contributes flavor and "tang" to the product. Other solvents include ethanol, methylene chloride, and halogenated hydrocarbons, such as the chlorinated-fluorinated hydrocarbons, including dichloromethane, tetrachloroethane, dichlorodifluoromethane; and the hydrocarbons, including cyclobutane. In most cases the solvents should have boiling points at atmospheric pressure, of 80° C. or less, for best gas-removing effects. A preferable range is from 40° or 50° to 70° C.

Other useful adjuvants include buffers, such as tetrasodium pyrophosphate, which also exerts a cleansing effect; preservatives, such as sodium benzoate, formaldehyde; bactericides; fungicides; and therapeutic materials, e.g., fluorine-containing compounds, which protect the teeth from decay. Examples of these are sodium fluoride, stannous fluoride, potassium fluoride, ammonium fluoride and complex fluorides, especially sodium monofluorophosphate. Antibacterial agents which are useful include $N^1$-(4-chlorobenzyl)-$N^5$-(2,4-dichlorobenzyl) biguanide; p-chlorophenyl biguanide; 4-chlorobenzhydrylguanylurea; 1,6-bis (2-ethylhexylbiguanide)hexane; 1,6-bis(p-chlorophenylbiguanido) hexane; and 5-amino-1,3-bis(2-ethylhexyl)-5-methylhexahydropyrimidine, and non-toxic acid addition salts thereof. Other useful adjuvants include coloring and whitening agents, dyestuffs, pigments, other preservatives, silicones, chlorophylls, ammoniated compounds, e.g., urea, diammonium phosphate, decorative suspended materials, e.g., finely ground mother-of-pearl, fillers (soluble salts), lubricants, e.g., mineral and other oils, and stabilizers for the compositions. Of course, with most of the adjuvants, the proportions used of insoluble materials having refractive indexes different from that of the balance of the dentifrice will be held low enough so that they do not interfere with the clarity of the product.

The gas used to form the bubbles in the dentifrice may be of any various suitable gases, with the main requirement being that it should not be so soluble in the dentifrice composition that the bubbles disappear into the composition by being dissolved therein. This is not to say that some solubility is not acceptable and may not in some cases be desirable. For example, if the solubility of the gas is low enough so that a proportion thereof is dissolved in the dentifrice, the bubbles may be decreased in size to a desirable range and it may be possible to utilize bubbling equipment which would not have to be so delicately controlled as to allow the insertion of microbubbles. Such a use of larger bubbles would be acceptable, due to their diminishing in size after being distributed in the dentifrice. However, it is normally preferred to employ gases which are soluble to an extent less than 10% in the dentifrice composition and those wherein the solubility is less than 5% appear to give best results. Among the useful gases that may be employed are included nitrogen, argon, and air. Of these, nitrogen is preferred but because of availability and because it yields almost the same results, air is often employed. In addition to these gases, others such as the aerosol propellants, which are halogenated hydrocarbons, may be used, providing that they are not too soluble. In this connection, it may be mentioned that carbon dioxide is sometimes useful and may contribute an effervescent or tangy effect to the dentifrice.

The proportions of the various dentifrice constituents employed will be such as to produce a satisfactorily extrudible gel or similar product which will be substantially form retaining after being discharged from a dispensing container. The product will contain a sufficient proportion of polishing agent to clean the teeth well but will not contain so much as to cause a gritty feeling or to interfere with the smoothness of the gel. Similarly, the vehicle present will be one which is compatible with the other constituents and will act as a medium in which they are dissolved or dispersed. The vehicle should not be present in such a large proportion as to make the product excessively fluid, or in such small proportion that the dentifrice loses its smooth attractive appearance. The detergent or foaming agent will be used in a small amount sufficient to contribute satisfactory foaming to aid in cleaning of the teeth, and not so much as to make the product cloudy or opaque. Similarly, the gelling agent present will thicken the dentifrice sufficiently to cause it to maintain its shape and to hold the gas bubbles in place therein at room temperature but there will not be so much present as to make the dentifrice rubbery, lumpy or opaque. The proportion of gelling agent employed will desirably raise the viscosity of the dentifrice to over 100,000 centipoises at 25° C. and preferably this will be over 200,000 or 1,000,000, centipoises. For materials which exhibit non-Newtonian characteristics, viscosity measurements may not be a true indication of thickness or the power to hold bubbles in place. In such cases, the product should be sufficiently firm so that, while it is extrudible at room temperature (25° C.), it holds the bubbles and does not allow them to collect in an uppermost section of the dentifrice in the container. For Newtonian fluids the centipoise figures given are measurements of such a satisfactory property. As will be described later, the viscosity, thickness or firmness of the composition should be less at elevated temperatures, so that globular gas bubbles may be formed at such temperatures even if the initial bubbles inserted into the dentifrice are not perfectly round.

The proportions of materials which are usually employed to obtain the properties described in the preceding paragraphs may vary over a wide range but experience has indicated certain ranges are most desirable to make best products. Thus, from 5 to 50% of polishing agent, 0.5 to 5% of gelling agent or thickener, 30 to 85% of polyhydric alcohol, 5 to 30% water and 0.5 to 5% of detergent or foaming agent will normally be employed. Preferred proportions are from 5 to 40% of polishing agent, 0.5 to 3% of gelling agent, 50 to 75% polyhydric alkanol(s), 10 to 20% water and 1 to 3% of detergent. In cases of opaque dentifrices, which may be made in accordance with the invented method, if desired, the proportion of polishing agent may be higher, from about 20 to 75%, the proportion of water may be higher, about 5 to 40% and that of polyhydric alkanol may be lower, usually being from 10 to 35%. Other materials and adjuvants may be present to contribute additional desirable properties for processing or final use. Thus, flavors and colorants make the dentifrice more pleasing to the user and solvents may facilitate preliminary degassing. Generally no more than 10% each of any such materials are employed and usually this will be 0.1 to 5% in most cases, preferably 0.1 to 3%, with the total such materials being less than 20%.

In the proportions described one may make excellent dentifrices of satisfactory bubble-holding properties. By following the method of the present invention bubbled dentifrices may be made which will be substantially clear despite interruptions in the product caused by both the gaseous and solid materials held therein. The impingement of the bubble against the solid does not alter its shape objectionably and there are no irregularities of appearance caused by changes in light paths through the product.

Although bubbles have been accidentally produced in dentifrices in the past, they have been considered to be disadvantageous and efforts have been made to remove them. This was because they were unattractive, irregular in shape, unevenly distributed and tended to cause density variations in the dentifrice. Also, in the case of clear dentifrices, bubbles can cause a cloudy appearance. By following the present method these disadvantages are avoided and a desirably clear dentifrice with bubbles attractively and evenly distributed therein is made.

As a first step in the manufacture of such a product, a dentifrice is produced which is substantially free of entrained gases and preferably, is also free of dissolved gases. Such degassing may be effected by any known techniques, usually with the aid of vacuum during the admixing of the various ingredients of the dentifrice or after the dentifrice has been prepared. The vacuums employed will normally be in the 500 to 730 millimeters of mercury range (30 to 260 mm. Hg absolute pressure) but higher vacuums, up to about 759 or 760 mm. Hg may also be used for faster degassing. If the finished dentifrice is to be degassed and preliminary vacuum operations are not effected, it may take as long as 2 to 3 hours to satisfactorily remove entrained and dissolved gases from the product. Such removal is facilitated by utilizing apparatuses such as Dopp, Unimix and Versator mixers, wherein thin films, e.g., less than 0.2 cm., of dentifrices are exposed to low pressure. Faster degassing is possible by subjecting the various constituents of premixes of the dentifrice to vacuums before and/or during admixing. Removal of gases is aided by the utilization of heat or volatile solvents (from 1 to 10%, preferably 1 to 5% of the latter, or volatile flavor, often being used), to thin the compositions and to promote the coalescence of gas bubbles and their removal. In a particularly preferred method, employed for the manufacture of clear gel dentifrices, heat, with or without the described vacuum, is used to degas or deaerate a mixture of polyalkanol and surface active agent (detergent or foaming agent) and this is admixed, under vaccum, with the rest of the previously degassed composition. The degassed intermediate is made by applying vacuum to a gelling agent-vehicle mixture, admixing with polishing agent and degassing during such admixture and after it. By following this method, which may be modified by the addition of solvents or flavoring agents which are volatile, having boiling points in the 40° to 70° C. range, an essentially gas free dentifrice is producible.

The gas free dentifrice is preferably at an elevated temperature or otherwise controlled so that its viscosity is sufficiently low to allow gases intentionally dispersed therein to form spherules. The dentifrices at this stage will be less viscous than when finally packed and at room temperature. Yet, it will be viscous enough so that the bubbles dispersed in it will not readily contact other such bubbles and will not be removed from the dentifrice or moved to one portion thereof. They will remain sufficiently dispersed for a long enough time to permit packing and cooling or other setting mechanism to produce the extrudible, yet form-retaining final product. Generally it is preferred to utilize heat as the thinning mechanism and to cool the product to set it but other techniques, such as utilizations of solvents and time-responsive setting agents may also be applied.

After making the substantially gas free dentifrice, which will preferably contain less gas than would be needed to produce one bubble 2 millimeters in diameter per cubic centimeter (less than ½% by volume), and preferably less than one bubble of 1 millimeter in diameter per c. cm., the dentifrice is adjusted in temperature or other variable is controlled to make it sufficiently thin to allow the formation of spherules by the injection of gas bubbles into it. Preferably, for Newtonian fluids, this corresponds to a viscosity of 25,000 centipoises or less, usually more than 1,000 cps. and preferably, more than 5,000 cps. At such viscosities, bubbles of gas to be dispersed in the dentifrice are controllably added and are distributed throughout the dentifrice, addition of bubbles continuing until the desired concentration is obtained, at which time the dentifrice is filled into an end use container such as toothpaste tubes, and is cooled in the container to set the gas bubbles in the dentifrice. The gas bubbles added are of equivalent spherical diameters in the range of 0.1 to 4 millimeters, preferably 1 to 4 mm. and most preferably from 2 to 3 mm. They are added until there are from 2 to 100 such bubbles per cubic centimeter dentifrice, preferably from 2 to 40 or 2 to 20 per c. cm.

Various methods of accurately producing bubbles of the mentioned sizes and of distributing them throughout the dentifrice may be employed but that considered to be simple, yet most effective is by the addition of bubbles through passages of approximately the desired final bubble diameter. The linear speeds of bubble addition, although usually in the range of 1 cm. to 50 cm./second, preferably over 0.1 meter/second, may be varied over a wider range, providing that the gas bubbles are broken off at the correct length to product spherules of the desired diameter. Thus, it is usually preferred that the passageways through which the gas enters the body of dentifrice should be set apart at least 1 or 2 diameters and the dentifrice should be moving by stirring or other agitation means in such a manner that a velocity component at right angles to the path of entry of the gas is at least twice the gas velocity at point of entry. This will shear off bubbles of length approximately the desired diameter and will prevent agglomeration. By adjustment of gas flows, by pressure alterations and dentifrice velocity modifications, and by changing mixer or circulator speeds, the sizes and concentrations of bubbles wanted are obtainable. Various types of mixers may be used but ordinary propeller, paddle, pump and circulating mixers are satisfactory. Of course, high shear or thin-film mixers are usually to be avoided. For good production rates the linear gas speed will be at least 0.1 m. per second and gas pressure, although low, will be regulated to obtain the right speed. The passageways through which the gas is added to the dentifrice may be individual fine tubes or may be embodied in a unitary member, such as a porous plate or a sparger. Mechanical breakup devices may also be employed to produce the bubbles but may not be as consistently accurate as the passageway method described. By conducting the operations, the technique of the invention and the modifications thereof to obtain particular products will be apparent to an equipment operator.

At the viscosities or thicknesses of the dentifrice to which the gas is being added at an elevated temperature, e.g., 30° to 60° C., the bubbles will not coalesce and are not interfered with by the dispersed insoluble polishing agent. The polishing agent particles, being less than 100 microns in diameter, preferably from 1 to 65 microns and most preferably from 1 to 20 microns, do not weaken the bubbles nor furnish sites for them to be joined to other bubbles, as might have been expected. It is considered that larger particles of the polishing agent are objectionable from this viewpoint and also because of their undesirably palpable nature. Because of the low content of gas in the dentifrice initially, few bubbles outside the desired size ranges are produced by temperature changes and because the gas addition is preferably undertaken at an elevated temperature, there is little tendency for bubble development on cooling, since gases are generally more soluble cold than hot. An advantage of the present dentifrices is the presence in the gas bubbles of volatilized materials, which may strengthen flavor taste and small sensations, at least with respect to those flavors whose effects are largely olfactory.

After manufacture the bubbled dentifrice is packed in is container as soon as possible, usually within an hour, preferably within 10 minutes. It is cooled to room temperature within an additional 5 hours, preferably in 2 hours, and is then ready for shipment.

Although the described method for making the gas-containing gel dentifrices is highly preferred, other methods may also be employed. This, in some circumstances bubbles may be dispersed mechanically by a mixer or may be generated chemically. The filling of cold product into the end use containers may be preferred in some operations and, providing that the bubbles are spherical at filling and that the equipment can handle the filling of the thickened product, good dentifrices may be produced by such a method. Also, the dentifrices may be vacuum packed, either by imposing a vacuum at the time of filling or by filling the heated dentifrice and causing the pressure to be decreased by contraction on cooling. In some instances, irregular bubbles may be intentionally created, and in such cases it may not be desirable to have the dentifrice at the time of gas addition in a sufficiently mobile state so as to produce gas spheres. The clear dentifrices of this invention may be made by the invented method or by other techniques, providing that the bubbles of gas are of a diameter in the 1 to 4 millimeter range and are distributed throughout the dentifrice so that there are from 2 to 20 bubbles per cubic centimeter of dentifrice, preferably regularly distributed, in clear gel dentifrices comprising an insoluble polishing agent, a gelling agent and a vehicle. In such products the gas which is dispersed preferably includes a major proportion of nitrogen and most preferably is nitrogen, although air is also satisfactory. Such dentifrices are highly preferably packed in clear plastic, e.g., polyvinyl chloride or polypropylene, transparent flexible tubes, are of a final viscosity over 200,000 cps. and contain 5 to 10 globular bubbles of 2 to 3 mm. diameter per cubic centimeter. Especially in those compositions wherein the polishing agent is sodium aluminosilicate of 1 to 20 microns diameter and a refractive index of 1.44 to 1.48, the gelling agent is a synthetic inorganic silicated clay of the Laponite type, the vehicle is an aqueous glycerol-sorbitol solution in which the ratio of glycerol:sorbitol is from 1:5 to 5:1, the proportions of constituents are from 5 to 50% polishing agents; 0.5 to 5% gelling agent; 30 to 85% of polyhydric alkanol; 5 to 30% water and 0.5 to 5% of foaming agent, superior products are obtained.

It is to be understood that in the preceding description, where individual materials of certain types have been mentioned, it is also within the contemplation of the invention that mixtures of such materials may be utilized to obtain best properties from each component.

The following examples illustrate but do not limit the invention. Unless otherwise indicated, all parts are by weight and all temperatures are in ° C.

EXAMPLE 1

| Components | Parts |
|---|---|
| Glycerine | 30 |
| Sorbitol (70% aqueous solution) | 33 |
| Laponite SP | 2 |
| Sodium aluminosilicate | 20 |
| Sodium N-lauroyl sarcoside | 2 |
| Flavoring (essential oils) | 1.0 |
| Synthetic sweetener (saccharin) | 0.1 |
| Coloring solution (1% aqueous, green dye) | 1.0 |
| Sodium monofluorophosphate | 0.8 |
| Water | 10.1 |

The sodium aluminosilicate employed is a complex having a refractive index of 1.47, a moisture content of about 10% and alumina content of 8% and contains 78% silica and 10% sodium oxide. Particle sizes are from 1 to 20 microns.

The Laponite SP, flavor, sweetener and coloring agent are mixed with approximately ⅓ of the glycerine and ⅓ of the sorbitol plus ½ of the water and a vacuum of 700 mm. Hg is applied for 10 minutes. Then, ⅓ of the glycerine and ⅓ of the sorbitol, together with ½ of the water are used to disperse the sodium aluminosilicate and sodium monofluorophosphate and a similar vacuum is applied to it for the same period of time to remove any entrained air. The sodium N-lauroyl sarcoside is next mixed in the remaining glycerine and sorbitol. The material is heated to 50° C. and held for 5 hours without the application of vacuum or for 10 minutes with the same vacuum previously mentioned. Then the polyhydric alkanol-gelling agent portion is mixed with the vehicle-polishing agent-fluoride portion, at a temperature of 40° C. with the application of 700 mm. Hg vacuum for 5 minutes, after which the surface active agent mixture is admixed, using the same vacuum and holding it for about 10 minutes. The mixing is done in a Unimix mixer, equipped with Teflon scraper blades which clear the walls of the mixture to within 0.2 mm., leaving only a very thin film of dentifrice thereon. The product resulting is essentially gas-free, containing less than 0.1% by volume of entrained air. The pH thereof is about 8. (Product pH's within the invention are 5–9). The product resulting is a visually clear gel dentifrice of attractive appearance.

Similar visually clear gas-free gel dentifrices are made by increasing the proportion of sorbitol so that it is 70% of the polyhydric alkanol content, replacing Laponite SP with 1 part of sodium carboxymethyl cellulose (adding sorbitol to make up for the other part of the Laponite omitted), replacing the sodium aluminosilicate with silica xerogel, (Syloid 63), replacing the sarcoside with sodium lauryl sulfate and replacing the sodium monofluorophosphate with 0.2 part of sodium fluoride, making up the additional 0.6 part with water. Such formula and the previously described one are degassed by holding under a vacuum of 740 mm. Hg for 4 hours while mixing in a Dopp mixer equipped with a following scraper to clear the inside walls thereof. All the products described, whether made by stepwise vacuum application, sometimes with the aid of heat, as in the deaeration of detergent mixture, or by final deaeration of the total dentifrice, are visually clear gels. In some cases the deaeration is intentionally terminated before completion so that the product contains a small proportion of air or nitrogen bubbles, e.g., a minor proportion, preferably less than 20% of the final bubble content of the dentifrice.

The dentifrices described are heated to 40° C. at which viscosities are in the 5,000 to 25,000 cps. range or equivalent thereto, so that gas bubbles added to the dentifrices become spherical in shape. Then, air is blown in through the bottoms of paddle mixers containing the various degassed dentifrice compositions, through a sparger having multiple passageways of 2 mm. diameter and set 1 cm. apart. The linear rate of flow of the air (nitrogen is used in some experiments) is 10 cm./second and the speed of the mixer is such that the average tangential velocity of the dentifrice relative to the air passageway at the point of exit of air therefrom is 50 cm./second. Air is added for about 1 minute, until there are about 10 bubbles per cubic centimeter of dentifrice, each bubble being about 2 mm. in diameter.

Within five minutes after addition of the air, the dentifrice is filled into transparent polyvinyl chloride tubes and within 2 hours thereafter it is cooled to 25° C., at which it has a viscosity of about 500,000 cps.

The products are packed and shipped and even after lengthy shelf lives, e.g., 6 months to 1 year, they are still attractive and useful dentifrices, are sparkling clear and contain the evenly distributed bubbles of air in the same locations as when manufactured.

In a variation of these experiments, Irish moss is employed instead of sodium carboxymethyl cellulose and ¼ of the foaming agent is replaced with Igepal CA-630 (nonyl phenoxy polyethoxy ethanol). A product of properties like the dentifrices previously described is obtained. Also, when a silica aerogel or pyrogenic silica is employed to supplement the gelling agent, in partial replacement thereof, usually less than 50%, the dentifrice resulting is also satisfactorily clear and the bubbles in it stand out as well. However, when the polishing agent is replaced with one of an index of refraction outside the 1.4 to 1.5 range or has particles thereof greater than 100 microns, it becomes apparent in the dentifrice and the clarity thereof is lost. In some cases, it is considered to be desirable to allow a small percentage of the weight of the polishing agent to be over 100 microns in size or outside the described permissible range of refractive indexes so as to make it apparent but in no case should the proportion thereof exceed 20% of the total polishing agent present. Although the vehicle may be entirely sorbitol or glycerol with some water, and in some cases water may be omitted entirely, with the product still being clear and holding the gas bubbles well dispersed therein, best results are obtained with the mixture of sorbitol, glycerol and water, sometimes with minor proportions of polypropylene glycol also being present. Instead of air, nitrogen, argon and Freons (chlorofluorinated lower alkanes) are used and good clear dentifrices also result.

EXAMPLE 2

A visually substantially clear dentifrice gel is prepared according to the following formula and any entrained air is removed by applying a vacuum of 700 mm. Hg for 2 hours, utilizing 2% of a solvent (ethanol, chloroform, or acetone) to assist in removal of the entrapped air bubbles. The formula used follows:

| Components | Parts |
| --- | --- |
| Sorbitol (70% aqueous solution) | 50 |
| Glycerine | 26 |
| Sodium aluminosilicate | 20 |
| Sodium lauryl sulfate | 2.0 |
| Flavor (oil of cloves) | 1.0 |
| Sodium carboxymethyl cellulose | 0.5 |
| Sodium saccharin | 0.1 |
| Formaldehyde | 0.1 |
| Aqueous coloring solution (1%) | 0.3 |

The sodium aluminosilicate used is a complex having a refractive index of 1.45, 10% moisture, 8% alumina, about 70% silica content, 7% sodium oxide, a particle size such that 98% of the particles are less than 30 microns in diameter and a loose bulk density of 0.114 g./cc. Utilizing the same apparatus described in Example 1, with individual passageway tubes having diameters of 1 mm. and being set apart by 5 mm., air is blown into the dentifrice until there are present about 20 bubbles per c. cm., each of about 1 mm. diameter. The bubbles are globular and within the times mentioned in Example 1, the dentifrice is filled into tubes and the tubes are cooled and sent to storage.

The products resulting are excellent clear dentifrices with the bubbles apparent in them. The bubbles are uniformly dispersed and are of approximately 1 mm. in diameter. In a variation of this experiment, instead of using the 1 mm. passageways, there are substituted 0.5 mm. and 3.0 mm. passageways, with approximately twice as many of the smaller passageways. By this technique there is obtained a dentifrice with a mixture of the two sizes of bubbles, 0.5 mm. and 3.0 mm. in diameter. In some cases, such mixtures are preferred, providing that the bubbles are globular and the distribution of the two different sized bubbles is even.

In variations of this experiment, argon is employed instead of air and the gels are tinted with different colors and flavored with different flavoring agents. In some cases, 1% of chloroform is included in the product for its flavoring effect. All such products are visually clear gels with excellently dispersed argon bubbles.

EXAMPLE 3

| Component | Parts |
| --- | --- |
| Glycerine | 25 |
| Sorbitol (70% aqueous solution) | 47 |
| Sodium aluminosilicate | 16 |
| Aerosil D-200 | 3 |
| Sodium N-lauroyl sarcoside | 2 |

| Component | Parts |
| --- | --- |
| Laponite SP | 2 |
| Flavor and sweetener | 1.2 |
| Aqueous coloring solution | 1 |
| Water | 2.8 |

The sodium aluminosilicate is a complex having a refractive index of 1.46, a moisture content of about 6%, an alumina content of 8.2%, a silica content of 72%, a sodium oxide content of 7%, an average particle size of about 20 microns and a sieved loose bulk density of about 0.07 g./cc.

When degassed according to the methods of Examples 1 and 2 and when aerated with air bubbles of 0.5 to 4 mm. in diameter, utilizing a diffuser for introduction of the air and otherwise following the methods of Examples 1 and 2, the product resulting is an acceptable visually clear dentifrice.

EXAMPLE 4

| Component | Parts |
| --- | --- |
| Glycerine | 23.9 |
| Sorbitol (70% aqueous solution) | 45 |
| Sodium carboxymethyl cellulose | 0.7 |
| Syloid 244 | 5 |
| Sodium aluminosilicate | 16 |
| Sodium lauryl sulfate | 2 |
| Sodium benzoate | 0.5 |
| Sodium saccharin | 0.2 |
| Aqueous coloring solution (1%) | 0.2 |
| Essential oil flavoring agent | 1.0 |
| Chloroform | 2.5 |
| Water | 3 |

The sodium aluminosilicate employed is that of Example 2. The product is made according to the method of Example 1 and results in a clear bubbled gel dentifrice of attractive appearance.

EXAMPLE 5

| Component | Parts |
| --- | --- |
| Glycerol | 25 |
| Sodium carboxymethyl cellulose (Hercules 12M31P) | 0.6 |
| Sodium benzoate | 0.5 |
| Sorbitol (70% aqueous solution) | 43.9 |
| Dye (1% aqueous solution) | 0.8 |
| Water, deionized | 3.0 |
| Sodium saccharin | 0.2 |
| Pyrogenic silica (Cab-O-Sil M-5) | 2.0 |
| Silica aerogel (Syloid No. 244) | 4.0 |
| Sodium aluminosilicate (DeGussa P820) | 16 |
| Sodium lauryl sulfate | 2.0 |
| Flavor (essential oils) | 1.0 |
| Chloroform | 1.0 |

A clear gel dentifrice is made according to the method of Example 1 and is found to be an excellent cleanser for the teeth, of attractive appearance and flavor, of good foaming power and excellent shelf stability. The bubbles are uniformly distributed therein and maintain their positions during a shelf life of 6 months in a transparent polyvinyl chloride flexible dispensing tube.

The invention has been described with respect to examples thereof but it will be clear that equivalents may be substituted for steps in the processes or components of the products without departing from the spirit of the invention.

What is claimed is:

1. An extrudible visually clear gel flavored dentifrice with strengthened flavor, taste and smell sensations, containing evenly distributed therein visible bubbles of gas containing volatilized flavor material and of diameter in the 1 to 4 millimeter range and distributed uniformly throughout the dentifrice so that there are from 2 to 40 bubbles per cubic centimeter of dentifrice, which dentifrice is of attractive appearance and comprises a transparent polishing agent which is of a refractive index matching that of the rest of the dentifrice, is insoluble in the rest of the dentifrice and is in particulate form, with the particles thereof being less than 100 microns in diameter, a gelling agent which is an organic or inorganic gum or thickener which produces a clear gel in the described composition, a vehicle which includes a polyhydric alcohol having a refractive index matching that of the other constituents, and a detergent or foaming agent, and is of a viscosity sufficient to maintain positions of the bubbles suspended therein during a shelf life of 6 months.

2. A dentifrice according to claim 1 wherein the bubbles are globular and are of air, the polishing agent is a complex aluminosilicate of an index of refraction in the range of 1.4 to 1.5 and of a particle size in the range of 1 to 65 microns, the gelling agent is an inorganic material, the vehicle includes sorbitol and the dentifrice includes a synthetic organic detergent, with the percentages of the mentioned components in the dentifrice being 5 to 50% of polishing agent, 0.5 to 5% of gelling agent, 30 to 85% of polyhydric alcohol vehicle and 0.5 to 5% of detergent, together with 5 to 30% of water, and the dentifrice made is of a viscosity greater than 100,000 centipoises at 25° C. and contains 2 to 20 bubbles per cc.

3. A dentifrice according to claim 1 wherein the bubbles are of diameters in the 2 to 3 mm. range and 5 to 10 are present per cc., the polishing agent is a sodium aluminosilicate of refractive index in the range of 1.44 to 1.48 and of particle sizes in the range of 1 to 20 microns diameter, the gelling agent is a silicated clay, the vehicle is a mixture of sorbitol and glycerol in a proportion within the range of 1:5 to 5:1 and the detergent is sodium N-lauroyl sarcoside, the percentages of the mentioned components in the dentifrice being 5 to 40% of polishing agent, 0.5 to 3% of gelling agent, 50 to 75% of polyhydric alcohol vehicle, 1 to 3% of detergent and 10 to 20% of water, and which is of a viscosity greater than 200,000 cps. at 25° C.

4. A product according to claim 1 made by a process wherein the gas-free or substantially gas-free viscous, extrudible gel dentifrice comprising polishing agent, gelling agent, vehicle and detergent or foaming agent is made and bubbles of gas of a size in the range of 1 to 4 mm. diameter of an equivalent sphere are mixed with the dentifrice, which is of a viscosity sufficient to maintain the bubbles suspended therein.

5. A product according to claim 1 made by a process which comprises degassing a gas-containing dentifrice gel and mixing with such degassed dentifrice gel, in clear state, gel-insoluble gas in bubble form.

6. A product according to claim 1 made by a process which comprises degassing a gas-containing dentifrice gel, mixing air with such degassed dentifrice gel, in clear state, at an elevated temperature and cooling the gel so as to increase the viscosity thereof sufficiently to maintain the gas bubbles suspended therein.

7. A product according to claim 2 made by a process which comprises degassing a gas-containing dentifrice gel, mixing air with such degassed dentifrice gel, in clear state, at an elevated temperature and cooling the gel so as to increase the viscosity thereof sufficiently to maintain the gas bubbles suspended therein.

* * * * *